United States Patent [19]

Eizember et al.

[11] 4,226,789

[45] Oct. 7, 1980

[54] REMOVAL OF NITROSAMINES FROM DENITROANILINES BY TREATMENT WITH HCL

[75] Inventors: Richard F. Eizember, Greenwood; Kathleen R. Vogler, Indianapolis; William N. Cannon, Cumberland, all of Ind.

[73] Assignee: Eli Lilly and Company, Indianapolis, Ind.

[21] Appl. No.: 54,345

[22] Filed: Jul. 2, 1979

Related U.S. Application Data

[63] Continuation of Ser. No. 878,834, Feb. 17, 1978, abandoned, which is a continuation-in-part of Ser. No. 816,558, Jul. 18, 1977, abandoned.

[51] Int. Cl.$^2$ .............................................. C07C 85/26
[52] U.S. Cl. .............................. 260/397.7 R; 260/577; 260/582
[58] Field of Search ........ 260/577, 582, 647, 583 CC, 260/397.7 R, 556 B

[56] References Cited

PUBLICATIONS

Fridman et al, "Russian Chem. Rev.", 40(1), pp. 34–50 (1971).
Zahradnick, "Chem. Listy", 51, pp. 937–945, (1957).
Wallis, "Lieb. Ann.", 345, pp. 277–288, (1906).
Smith, "The Chem. of Open-Chain Org. Nitrogen Cmpds", pp. 470–474, (1966).
Sidgwick, "The Org. Chem of Nitrogen", pp. 592–594, (1966).
Biggs et al. "J. Chem. Soc., Perkin Trans. II", pp. 107–111, (1975).
Biggs et al. "J. Chem. Soc., Perkin Trans. II", pp. 601–605, (1976).

*Primary Examiner*—John Doll
*Attorney, Agent, or Firm*—Kathleen R. S. Page; Arthur R. Whale

[57] ABSTRACT

The present invention is directed to a process for the removal of nitrosamines from dinitroanilines.

78 Claims, No Drawings

REMOVAL OF NITROSAMINES FROM DENITROANILINES BY TREATMENT WITH HCL

CROSS REFERENCE TO RELATED APPLICATION

This is a continuation of application Ser. No. 878,834 filed Feb. 17, 1978 and abandoned after the filing of the present application. Application Ser. No. 878,834 is a continuation-in-part of application Ser. No. 816,558, filed July 18, 1977, and abandoned after the filing of application Ser. No. 878,834.

SUMMARY

The dinitroaniline class of compounds includes numerous commercial herbicides. Recently a new analytical device, known as a thermal energy analyzer (TEA), has been developed (*J. Chromatogr.* 107 (1975), 351 and references there cited; and "N-Nitroso Compounds in the Environment," IARC Scientific Publication #9 (International Agency for Research on Cancer, Lyon, 1974), p. 40). The TEA analyzes specifically for the nitroso (—NO) group, and is capable of detecting the nitroso group at concentrations as low as 0.02 ppm— much lower than prior analytical techniques. Analysis of various dinitroanilines by the TEA reveals that some of the dinitroanilines contain very small amounts of nitrosamines. The presence of even a very small amount of nitrosamine is viewed as undesirable, because certain of the nitrosamines have been shown to be carcinogenic in animals.

The present invention provides a method for removing nitrosamines from dinitroanilines.

DETAILED DESCRIPTION

The present invention is directed to a process which comprises contacting a nitrosamine-containing dinitroaniline in liquid phase with a reagent selected from the group consisting of hydrochloric acid and gaseous HCl, until the concentration of the nitrosamine has been reduced; and thereafter recovering the dinitroaniline. Dinitroanilines with which the present invention can be practiced (and their generic names where available) are (1) 4-trifluoromethyl-2,6-dinitro-N,N-di-n-propylaniline (trifluralin);
(2) 4-isopropyl-2,6-dinitro-N,N-di-n-propylaniline (isopropalin);
(3) 4-trifluoromethyl-2,6-dinitro-N-n-butyl-N-ethylaniline (benefin);
(4) 4-trifluoromethyl-2,6-dinitro-N-ethyl-N-methallylaniline (ethalfluralin);
(5) 4-tert-butyl-2,6-dinitro-N-sec-butylaniline (butralin);
(6) 3,4-dimethyl-2,6-dinitro-N-(1-ethylpropyl)aniline (pendimethalin);
(7) 4-trifluoromethyl-2,6-dinitro-N-propyl-N-(2-chloroethyl)aniline (fluchloralin);
(8) 4-trifluoromethyl-2,6-dinitro-N-propyl-N-(cyclopropylmethyl)aniline (profluralin);
(9) 4-trifluoromethyl-2,6-dinitro-3-amino-N,N-diethylaniline (dinitramine);
(10) 4-trifluoromethyl-2,6-dinitro-3-chloro-N,N-diethylaniline (intermediate to dinitramine);
(11) 4-methyl-2,6-dinitro-N,N-bis(2-chloroethyl)aniline;
(120 4-sulfamoyl-2,6-dinitro-N,N-di-n-propylaniline (oryzalin); and
(13) 4-(methylsulfonyl)-2,6-dinitro-N,N-di-n-propylaniline (nitralin).

Preferred dinitroanilines with which the present invention is carried out are trifluralin, isopropalin, benefin, and ethalfluralin.

Generally, the dinitroanilines are prepared by a reaction route of which the following, for trifluralin, is typical:

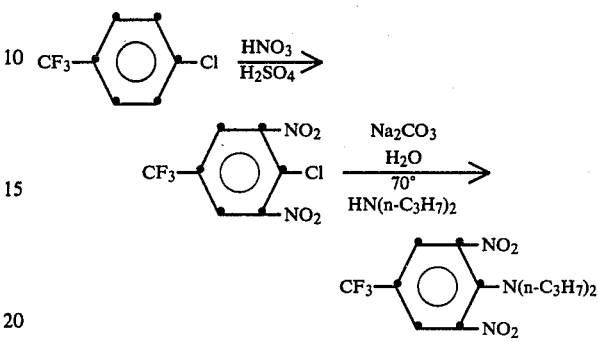

It is believed that small amounts of nitrogen oxides remaining from the nitration step react with a portion of the amine during the amination step, generating small amounts of nitrosamine which may appear in the final dinitroaniline product. Therefore, any nitrosamine contaminant is expected to be the nitroso derivative of the alkylamine employed. However, it is conjectured that exceedingly small amounts of yet other nitrosamines may also be formed. The removal of nitrosamines, regardless of identity, is desirable, and the present process meets that objective.

The mechanism by which the present process operates is not known with certainty, but it is believed that HCl denitrosates the nitrosamine to some other species, probably the HCl salt of the corresponding amine. It is also believed but not yet proven that NOCl may be generated as part of the denitrosation. In any event, the net result is conversion of the undesirable nitrosamine to a water soluble substance which can readily be removed from the dinitroaniline.

The present process provides substantial reduction in nitrosamine concentration, regardless of the initial amount of nitrosamine. The process has been conducted with dinitroanilines containing from as little as about 10 ppm of nitrosamine to as much as several thousand ppm of nitrosamine; nitrosamine concentration is generally reduced to about one-tenth of the initial amount, or less. In many cases, the nitrosamine concentration is reduced to less than about 1 ppm.

The present process is conducted in a liquid phase. In the instance of many of the dinitroanilines, this can be achieved by heating the nitrosamine-containing dinitroaniline to its melting temperature or higher and conducting the reaction neat. A liquid phase can also be achieved by dissolving the nitrosamine-containing dinitroaniline in a solvent. Suitable solvents include alcohols such as ethanol; ketones such as acetone; and hydrocarbons, both aliphatic and aromatic. Solvents comprising moieties reactive with HCl should be avoided. For example, secondary and tertiary alcohols should be avoided because of their reactivity with HCl.

The reagent to be employed in the present process is either hydrochloric acid or gaseous HCl. If hydrochloric acid is used, it should contain at least 20% HCl (by weight). Better results have been obtained with more concentrated hydrochloric acid, such as 33–38%. Gaseous HCl can also be employed, and this is generally a preferred mode of carrying out the present invention. In the instance of ethalfluralin, gaseous HCl has an advantage over hydrochloric acid of avoiding addition across the methallyl double bond.

The amount of hydrochloric acid or gaseous HCl to be employed is not critical, so long as the amount is effective to reduce the initial amount of nitrosamine to a lesser amount. With hydrochloric acid, 0.04 gram per 100 grams of dinitroaniline has been found satisfactory. Similarly, employing gaseous HCl, 250 ml. per 100 grams of dinitroaniline has been found satisfactory. Larger amounts (by 3X) have also worked satisfactorily but have provided no advantage. In laboratory scale reactions with gaseous HCl, addition rates of 5–90 ml./min./100 grams of dinitroaniline have been satisfactorily employed. Rates of 8–12 ml./min/100 grams of dinitroaniline are preferred.

The reaction can be conducted at temperatures over a wide range. In general, temperatures below about 140° C. are employed, and temperatures below about 100° C. are preferred because of the greater risk of side reactions at higher temperatures. When conducting the process in a solvent, satisfactory temperatures vary widely with the identity of the solvent, but generally range from room temperature to about 100° C. When conducting the process neat, the reaction is conducted at temperatures above the melting temperature of the particular dinitroaniline. Good results have been achieved at temperatures of from 70° to 90° C. when conducting the process neat with trifluralin (m.p., 54°–5° C.), isopropalin (m.p., 30° C.), benefin (m.p., 65°–6° C.), and ethalfluralin (m.p., 57°–9° C.).

The reaction can be conducted at atmospheric pressures or at elevated pressures. It has been found to be advantageous to conduct the reaction with gaseous HCl at 70°–90° C., and with 1–10 psig, and preferably 3–5 psig, of HCl gas pressure.

The presence of water in the nitrosamine-containing dinitroaniline has a deleterious effect on the present process. This is especially true when employing gaseous HCl in that more HCl is required for denitrosation. Therefore, when employing gaseous HCl, it is preferred that the nitrosamine-containing dinitroaniline be relatively dry, such as less than 0.2 percent of water.

The rate at which the present process proceeds will vary with the concentration of the nitrosamine, temperature, the form of HCl reagent, the rate of its addition, and other factors. The progress of nitrosamine removal can be monitored by gas chromatography or by TEA analysis. Denitrosation is generally complete in less than an hour. Time studies of the present process have shown an early drop in levels of nitrosamine, followed in some instances by a slight rise in levels of nitrosamine upon extended reaction time. It is believed that extended exposure of (1) the dinitroaniline and (2) the conjectured alkylamine denitrosation product, to the reaction conditions may result in further nitrosamine formation. Therefore, minimizing reaction times is desirable.

Workup of the reaction mixture is carried out by conventional procedures. The workup desirably takes the form of a water wash followed by a slightly basic wash to assure removal of traces of HCl. Provision should also be made, during the course of the present denitrosation process, for the removal of by-product gases.

The following examples illustrate the present invention and will enable those skilled in the art to practice the invention.

Unless otherwise noted, determination of nitrosamine concentration in the following examples was done by a gas chromatographic method sensitive down to about 0.5 ppm. A "non-detectable" reading (reported below as "N.D.") was considered to represent less than about 0.5 ppm of nitrosamine. A Hewlett-Packard Model 5711A gas chromatograph was used but the method can be carried out with any gas chromatograph apparatus equipped with a flame ionization detector. The column was a glass coil 4 ft.×⅛ inch i.d., packed with 3% Carbowax 20 M on 100/120 mesh AW DMCS Chromosorb G operated at 100° C. After the nitrosamine peak eluted, the column was heated to 230° C. and held there for about 15 minutes. The helium flow rate was 60 ml./min. A standard was employed of approximately the same concentration of the nitrosamine expected of the sample. Both standard and sample were prepared in methylene chloride.

Those examples utilizing TEA analysis are so indicated. Analyses by this method were carried out in essentially the same procedures as described at *J. Chromatogr.* 109 (1975), 271. In the context of the present invention, this method is considered to be sensitive to nitrosamine concentrations as low as 0.05 ppm. Where TEA analysis of the samples reported below showed no nitrosamine, it is reported as "N.D."

In Example 2, a gas chromatography-mass spectrometry method of analysis is reported. In this method, samples were dissolved in benzene and purified by alumina column chromatography using benzene as the eluting solvent. The nitrosamine content of the sample was measured on an LKB-9000 gas chromatograph-mass spectrometer equipped with a 5% Carbowax 20 M column. The column temperature was adjusted to 130° C. which resulted in a retention time of two minutes for nitrosodi-n-propylamine. It was detected by adjusting the magnet to the molecular ion (m/e=130) and displaying the resulting ion current on a strip chart recorder.

EXAMPLE 1: NITROSAMINE REMOVAL FROM TRIFLURALIN, 20% HYDROCHLORIC ACID, ETHANOL SOLVENT

Trifluralin (30 grams), containing 256 ppm. of nitrosamine, was mixed with 20 ml. of 20% hydrochloric acid and 5 ml. of ethanol. The mixture was heated to 90° C. and maintained at that temperature, with stirring, for 3 hours. The layers were separated and the organic layer washed with 10 percent sodium bicarbonate. The product was analyzed for nitrosamine; none could be detected.

EXAMPLE 2: NITROSAMINE REMOVAL FROM TRIFLURALIN, HCL GAS, BENZENE SOLVENT

Trifluralin (10 grams of a sample containing 480 ppm. of nitrosamine) was dissolved in 200 ml. of benzene and the solution stirred and heated to reflux (80° C.). HCl gas was passed into the refluxing solution continuously over a period of an hour. The reaction mixture was cooled slightly and washed twice, each time with an equal volume of water. The benzene layer was separated, dried over anhydrous magnesium sulfate, and filtered, and the benzene was removed on a rotary evaporator. The resulting trifluralin was analyzed for nitrosamine content by a gas chromatography-mass spectrometry method. Analysis showed <1 ppm of nitrosamine.

EXAMPLE 3: NITROSAMINE REMOVAL FROM TRIFLURALIN, HCL GAS

Trifluralin (50 grams) was heated to 70° C. HCl gas was bubbled through at a rate of 8–12 ml./min. Samples were taken at 0, 30, and 60 minutes. Each sample was washed with 10 percent sodium carbonate solution, dried and analyzed for nitrosamine content. The results were as follows:

| time when sample taken | nitrosamine concentration |
| --- | --- |
| 0 | 32.6 ppm. |
| 30 min. | 2.9 ppm. |
| 60 min. | N.D. |

EXAMPLE 4: NITROSAMINE REMOVAL FROM BENEFIN, 38% HYDROCHLORIC ACID

Benefin (15 grams), containing 130 ppm. of nitrosamine, was heated to 70° C. Concentrated (38%) hydrochloric acid (1.5 gram) was added and the reaction mixture was stirred for 15 minutes. The organic layer was separated and washed with a 10% sodium carbonate solution. The nitrosamine content of the resulting product was 17 ppm.

EXAMPLE 5: NITROSAMINE REMOVAL FROM BENEFIN, HCL GAS

Benefin (25 grams), containing 130 ppm of nitrosamine, was heated to 70° C. HCl gas was bubbled through at a rate of 8–12 ml./min. Samples were taken at 10, 20, 30 minutes. Each sample was washed with 10 percent sodium carbonate solution and analyzed for nitrosamine content. The results were as follows:

| time when sample taken | nitrosamine concentration |
| --- | --- |
| 10 min. | 65 ppm. |
| 20 min. | 38 ppm. |
| 30 min. | 14 ppm. |

EXAMPLE 6: NITROSAMINE REMOVAL FROM ETHALFLURALIN, HCL GAS

Ethalfuralin (100 grams) was heated to 70° C. HCl gas was bubbled through at a rate of 90 ml./min. Samples were taken periodically. Each sample was washed with 2 ml. of 10% sodium carbonate solution, dried, and analyzed for nitrosamine content. The results were as follows:

| time when sample taken | nitrosamine concentration |
| --- | --- |
| 0 | 10.2 ppm. |
| 15 min. | N.D. |
| 30 min. | N.D. |
| 1 hour | N.D. |

EXAMPLE 7: NITROSAMINE REMOVAL FROM TRIFLURALIN, FASTER RATE OF ADDITION OF HCL GAS

Trifluralin (50 grams) was washed with water for 30 minutes, and air-dried for 30 minutes. It was then heated to 70° C. and HCl gas bubbled through at a rate of 35 ml./min. Samples were taken at 0, 15, 30, and 60 minutes. Each sample was washed with 10% sodium carbonate and analyzed for nitrosamine content. The results were as follows:

| time when sample taken | nitrosamine concentration |
| --- | --- |
| 0 | 9.3 ppm. |
| 15 min. | <1 |
| 30 min. | <1 |
| 1 hour | <1 |

EXAMPLE 8: NITROSAMINE REMOVAL FROM TRIFLURALIN, HCl GAS, EFFECT OF ADDED $H_2O$

Trifluralin (100 grams) was heated to 70° C. and 0.5 ml. of water was added. HCl gas was then bubbled in at a rate of 8 Zml./min. Samples were taken periodically; each was washed with 10 percent sodium carbonate solution, dried, and analyzed for nitrosamine content. The results were as follows:

| time when sample taken | nitrosamine concentration |
| --- | --- |
| 0 | 27 ppm. |
| 10 min. | 14 ppm. |
| 20 min. | 6.8 ppm. |
| 30 min. | 3.2 ppm. |
| 45 min. | N.D. |

EXAMPLE 9: NITROSAMINE REMOVAL FROM TRIFLURALIN, HCL GAS OVER LONGER TIME

Trifluralin (100 grams) was heated to 70° C. HCl gas was bubbled through at a rate of 8–12 ml./min. Samples were taken every 2 hours. Each sample was washed with 10% sodium carbonate solution, dried and analyzed for nitrosamine content. The results were as follows:

| time when sample taken | nitrosamine concentration |
| --- | --- |
| 0 | 48 ppm. |
| 2 hours | N.D. |
| 4 hours | N.D. |
| 6 hours | N.D. |
| 8 hours | 1.3 ppm. |

EXAMPLE 10: NITROSAMINE REMOVAL FROM ETHALFLURALIN, 38% HYDROCHLORIC ACID

Ethalfluralin (85 grams), containing 9 ppm. of nitrosamine by TEA analysis, was heated to 70° C.; concentrated hydrochloric acid (38%; 15 grams) added, and the reaction mixture stirred for 30 minutes. The layers were separated and the organic layer was washed with 15 ml. of water. The layers were again separated and the organic layer washed with 15 ml. of 10% sodium carbonate solution and then with 15 ml. of water. The organic layer was dried at 120° C. for 15 minutes. A sample was analyzed by TEA; no nitrosamine was detected.

EXAMPLE 11: NITROSAMINE REMOVAL FROM TRIFLURALIN, HCL GAS, FASTER RATE OF ADDITION

Trifluralin (50 grams), containing 18 ppm. of nitrosamine, was heated to 70° C. HCl gas was bubbled in at a rate of 90 ml./min. for 5 minutes. The trifluralin was then washed with 5 ml. of 10% sodium carbonate and dried. A sample analyzed for nitrosamine content showed none detectable.

EXAMPLE 12: NITROSAMINE REMOVAL FROM TRIFLURALIN, 38% HYDROCHLORIC ACID OVER LONGER TIME

Trifluralin (60 grams) was heated to 70° C. Concentrated hydrochloric acid (38%, 6 grams) was added and the reaction mixture stirred. Samples were taken at intervals and analyzed for nitrosamine content. The results were as follows:

| time when sample taken | nitrosamine concentration |
| --- | --- |
| 0 | 10 ppm |
| 30 min. | 1.4 ppm. |
| 1 hour | 1.5 ppm. |
| 2 hours | <1 ppm. |
| 3 ½ hours | 1.4 ppm. |
| 4 hours | 1.4 ppm. |

EXAMPLE 13: NITROSAMINE REMOVAL FROM TRIFLURALIN, HCL GAS AT HIGHER TEMPERATURE

Trifluralin (100 grams) was dried for 30 minutes at 120° C. with air blowing over the surface. HCl gas was then passed through at a rate of 12 ml./min. and a temperature of 85° C. Samples, each 10 grams, were taken at 20, 40, 60, and 90 minutes. Each sample was washed with 5 ml. of 5% sodium carbonate solution and dried on a rotary evaporator for 15 minutes at 90° C. Results were as follows:

| time when sample taken | nitrosamine concentration |
| --- | --- |
| 0 | 11.1 ppm. |
| 20 min. | N.D. |
| 40 min. | N.D. |
| 60 min. | N.D. |
| 90 min. | N.D. |

EXAMPLE 14: NITROSAMINE REMOVAL FROM ISOPROPALIN, HCL GAS AND ELEVATED PRESSURE

To 1 liter of a xylene solution of isopropalin (representing about 700 grams of isopropalin containing by TEA analysis 22 ppm. of nitrosamine) gaseous HCl was added to a pressure of 5 psig and at a temperature of 70° C. Samples were periodically withdrawn; each was washed with 50% by volume of a 5% sodium carbonate solution, the layers separated, and the organic layer dried for 10 minutes at 60° C. on a rotary evaporator. The results by TEA analyses were as follows:

| time when sample taken | nitrosamine concentration |
| --- | --- |
| 0 | 22 ppm. |

-continued

| time when sample taken | nitrosamine concentration |
| --- | --- |
| 30 min. | .22 ppm. |
| 60 min. | .19 ppm. |
| 90 min. | .4 ppm. |
| 120 min. | .52 ppm. |
| 2 hours, 30 min. | .40 ppm. |
| 3 hours | .28 ppm. |
| 3 hours, 30 min. | .24 ppm. |

EXAMPLE 15: NITROSAMINE REMOVAL FROM ETHALFLURALIN, HCL GAS

Ethalfluralin (100 grams), containing 10.5 ppm. of nitrosamine, was heated to 70° C. and HCl gas was bubbled in at a rate of 8 ml./min. Samples were removed periodically and analyzed for nitrosamine content by the thermal energy analyzer. Results were as follows:

| time when sample taken | nitrosamine concentration |
| --- | --- |
| 10 min. | 10.9 ppm. |
| 20 min. | 6.6 ppm. |
| 30 min. | N.D. |
| 40 min. | N.D. |

EXAMPLE 16: NITROSAMINE REMOVAL FROM TRIFLURALIN, 38% HYDROCHLORIC ACID RECYCLED

Trifluralin (100 grams), containing 18 ppm. of nitrosamine, was heated to 70° C. and 20 grams of 38% hydrochloric acid was added. The reaction mixture was stirred at 70° C. for 30 minutes. The layers were then separated. The organic layer was washed with 10 ml. of 10% sodium carbonate solution and analyzed for nitrosamine concentration. The acid layer was saturated with HCl gas and used in another nitrosamine reaction with another 100 grams of trifluralin, conducted under the same conditions as described above (the first recycle). Two more recycles of the acid were made. Results were as follows:

| Sample | Nitrosamine Concentration |
| --- | --- |
| control (starting trifluralin) | 18 ppm. |
| first acid treatment | N.D. |
| first recycle | N.D. |
| second recycle | N.D. |
| third recycle | N.D. |

EXAMPLE 17: NITROSAMINE REMOVAL FROM TRIFLURALIN, HCL GAS AND ELEVATED PRESSURE IN PILOT PLANT RUN

Trifluralin (210.0 kilograms) was melted overnight (about 20 hours) at 70° C. and charged into a 75 gallon glass-lined still. The trifluralin was then heated to 90° C. and HCl gas passed in under pressure. The reaction conditions were as follows:

| Time | Temp. (C) | HCl psig | Sample # | Nitrosamine Concentration |
| --- | --- | --- | --- | --- |
| 0 | 90° | 0 | #1 | 22 ppm |

| Time | Temp. (C) | HCl psig | Sample # | Nitrosamine Concentration |
|---|---|---|---|---|
| 8 min. | 91 | 2.5 | #2 | 3 ppm |
| 16 min. | 90 | 2.5 | #3 | N.D. |
| 22 min. | 89 | 2.5 | #4 | N.D. |
| 39 min. | 90 | 2.5 | #5 | N.D. |
| 65 min. | 90 | 2.5 | #6 | N.D. |
| 71 min. | 90 | 2.5 | #7 | N.D. |

Thereafter the reaction mixture was neutralized with sodium carbonate and another sample taken; no nitrosamine could be detected.

Total HCl used was 0.38 kilogram.

EXAMPLE 18: NITROSAMINE REMOVAL FROM TRIFLURALIN, HCL GAS, ETHANOL SOLVENT

HCl gas was bubbled (12 ml./min.) into a mixture of trifluralin (50 ml.) and ethanol (25 ml.) at 70° C. Samples were taken at 30 minutes and at 1 hour. Each sample was worked up by stripping on a rotary evaporator for 15 minutes at 30° C., and then washing with 5 ml. of 5 percent sodium carbonate solution. The layers were separated and the organic layer was stripped on a rotary evaporator for 15 minutes at 90° C. Results were as follows:

| time when sample taken | nitrosamine concentration |
|---|---|
| 0 | 44 ppm. |
| 30 min. | 20 ppm. |
| 60 min. | 14 ppm. |

EXAMPLE 19: NITROSAMINE REMOVAL FROM TRIFLURALIN, TWO TREATMENTS WITH 38% HYDROCHLORIC ACID

Trifluralin (20 grams), containing 68 ppm. of nitrosamine, and 5 ml. of 38% hydrochloric acid were mixed and held with stirring at 70° C. for 20 minutes. The layers were then separated, and to the organic layer, another 5 ml. of 38% hydrochloric acid were added. The reaction mixture was again maintained at 70° C. for 20 minutes with stirring. The layers were separated and the organic layer washed with 10 ml. of 10% sodium carbonate. The product was analyzed for nitrosamine content. None was detectable by gas chromatography or TEA.

EXAMPLE 20: NITROSAMINE REMOVAL FROM DINITRAMINE, HCL GAS

Dinitramine (10 grams of a sample containing 138 ppm of nitrosamine) was heated to about 110° C. and HCl gas added at a rate of about 35 ml./min. for 45 minutes. After a 2 gram sample (labelled Sample 1) was removed, the hot remaining liquid was added slowly to 60 ml. of methylene chloride. 15 ml. of 10 percent sodium carbonate solution was added. The organic phase was separated and solvent removed from it on a rotary evaporator for 15 minutes at 45° C., yielding 8 grams of yellow solid (labelled Sample 2).

Each sample was analyzed for nitrosamine content by TEA. Results were as follows:

| Sample | Nitrosamine Concentration |
|---|---|
| 1 | <0.2 |
| 2 | <0.2 |

We claim:
1. The process which comprises
   (1) contacting a nitrosamine-containing dinitroaniline selected from the group consisting of
   trifluralin
   isopropalin,
   benefin,
   ethalfluralin,
   butralin,
   pendimethalin,
   fluchloralin,
   profluralin,
   dinitramine,
   4-trifluoromethyl-2,6-dinitro-3-chloro-N,N-diethylaniline,
   4-methyl-2,6-dinitro-N,N-bis(2-chloroethyl)aniline,
   oryzalin, and
   nitralin,
   (a) in liquid phase
   (b) with a reagent selected from the group consisting of 20-38% hydrochloric acid and gaseous HCl until the concentration of the nitrosamine has been reduced from about several thousand ppm or less; and
   (2) thereafter recovering the dinitroaniline.
2. The process of claim 1 in which the dinitroaniline is trifluralin, isopropalin, benefin, or ethalfluralin.
3. The process of claim 2 in which the dinitroaniline is trifluralin.
4. The process of claim 2 in which the dinitroaniline is isopropalin.
5. The process of claim 2 in which the dinitroaniline is benefin.
6. The process of claim 2 in which the dinitroaniline is ethalfluralin.
7. The process of claim 2 in which the reagent is 20-38% hydrochloric acid.
8. The process of claim 7 in which the reagent is 33-38% hydrochloric acid.
9. The process of claim 8 conducted at temperatures of 70°-90° C.
10. The process of claim 9 in which the dinitroaniline is trifluralin.
11. The process of claim 9 in which the dinitroaniline is isopropalin.
12. The process of claim 2 in which the reagent is gaseous HCl.
13. The process of claim 12 conducted neat.
14. The process of claim 13 conducted at temperatures of 70°-90° C.
15. The process of claim 14 in which the dinitroaniline is trifluralin.
16. The process of claim 14 in which the dinitroaniline is isopropalin.
17. The process of claim 14 in which the dinitroaniline is benefin.
18. The process of claim 14 in which the dinitroaniline is ethalfluralin.
19. The process of claim 14 employing 3-5 psig of HCl gas pressure.

20. The process of claim 19 in which the dinitroaniline is trifluralin.

21. The process of claim 1 in which the dinitroaniline is butralin.

22. The process of claim 1 in which the dinitroaniline is pendimethalin.

23. The process of claim 1 in which the dinitroaniline is fluchloralin.

24. The process of claim 1 in which the dinitroaniline is profluralin.

25. The process of claim 1 in which the dinitroaniline is dinitramine.

26. The process of claim 1 in which the dinitroaniline is 4-trifluoromethyl-2,6-dinitro-3-chloro-N,N-diethylaniline.

27. The process which comprises
 (1) contacting a nitrosamine-containing dinitroaniline selected from the group consisting of
   trifluralin,
   isopropalin,
   benefin,
   ethalfluralin,
   butralin,
   pendimethalin,
   fluchloralin,
   profluralin,
   dinitramine,
   4-trifluoromethyl-2,6-dinitro-3-chloro-N,N-diethylaniline,
   4-methyl-2,6-dinitro-N,N-bis(2-chloroethyl)aniline,
   oryzalin, and
   nitralin,
   (a) in liquid phase
   (b) with a reagent selected from the group consisting of 20-38% hydrochloric acid and gaseous HCl until the concentration of the nitrosamine has been reduced from about 480 ppm or less; and
 (2) thereafter recovering the dinitroaniline.

28. The process of claim 27 in which the dinitroaniline is trifluralin, isopropalin, benefin, or ethalfluralin.

29. The process of claim 28 in which the dinitroaniline is trifluralin.

30. The process of claim 28 in which the dinitroaniline is isopropalin.

31. The process of claim 28 in which the dinitroaniline is benefin.

32. The process of claim 28 in which the dinitroaniline is ethalfluralin.

33. The process of claim 28 in which the reagent is 20-38% hydrochloric acid.

34. The process of claim 34 in which the reagent is 33-38% hydrochloric acid.

35. The process of claim 34 conducted at temperatures of 70°-90° C.

36. The process of claim 35 in which the dinitroaniline is trifluralin.

37. The process of claim 35 in which the dinitroaniline is isopropalin.

38. The process of claim 28 in which the reagent is gaseous HCl.

39. The process of claim 38 conducted neat.

40. The process of claim 39 conducted at temperatures of 70°-90° C.

41. The process of claim 40 in which the dinitroaniline is trifluralin.

42. The process of claim 40 in which the dinitroaniline is isopropalin.

43. The process of claim 40 in which the dinitroaniline is benefin.

44. The process of claim 40 in which the dinitroaniline is ethalfluralin.

45. The process of claim 40 employing 3-5 psig of HCl gas pressure.

46. The process of claim 45 in which the dinitroaniline is trifluralin.

47. The process of claim 27 in which the dinitroaniline is butralin.

48. The process of claim 27 in which the dinitroaniline is pendimethalin.

49. The process of claim 27 in which the dinitroaniline is fluchloralin.

50. The process of claim 27 in which the dinitroaniline is profluralin.

51. The process of claim 27 in which the dinitroaniline is dinitramine.

52. The process of claim 27 in which the dinitroaniline is 4-trifluoromethyl-2,6-dinitro-3-chloro-N,N-diethylaniline.

53. The process which comprises
 (1) contacting a nitrosamine-containing dinitroaniline selected from the group consisting of
   trifluralin,
   isopropalin,
   benefin,
   ethalfluralin,
   butralin,
   pendimethalin,
   fluchloralin,
   profluralin,
   dinitramine,
   4-trifluoromethyl-2,6-dinitro-3-chloro-N,N-diethylaniline,
   4-methyl-2,6-dinitro-N,N-bis(2-chloroethyl)aniline,
   oryzalin, and
   nitralin,
   (a) in liquid phase
   (b) with a reagent selected from the group consisting of 20-38% hydrochloric acid and gaseous HCl until the concentration of the nitrosamine has been reduced from about 480 ppm or less to about 1 ppm or less; and
 (2) thereafter recovering the dinitroaniline.

54. The process of claim 53 in which the dinitroaniline is trifluralin, isopropalin, benefin, or ethalfluralin.

55. The process of claim 54 in which the dinitroaniline is trifluralin.

56. The process of claim 54 in which the dinitroaniline is isopropalin.

57. The process of claim 54 in which the dinitroaniline is benefin.

58. The process of claim 54 in which the dinitroaniline is ethalfluralin.

59. The process of claim 54 in which the reagent is 20-38% hydrochloric acid.

60. The process of claim 59 in which the reagent is 33-38% hydrochloric acid.

61. The process of claim 60 conducted at temperatures of 70°-90° C.

62. The process of claim 61 in which the dinitroaniline is trifluralin.

63. The process of claim 61 in which the dinitroaniline is isopropalin.

64. The process of claim 54 in which the reagent is gaseous HCl.

65. The process of claim 64 conducted neat.

66. The process of claim 65 conducted at temperatures of 70°–90° C.

67. The process of claim 66 in which the dinitroaniline is trifluralin.

68. The process of claim 66 in which the dinitroaniline is isopropalin.

69. The process of claim 66 in which the dinitroaniline is benefin.

70. The process of claim 66 in which the dinitroaniline is ethalfluralin.

71. The process of claim 66 employing 3–5 psig of HCl gas pressure.

72. The process of claim 71 in which the dinitroaniline is trifluralin.

73. The process of claim 53 in which the dinitroaniline is butralin.

74. The process of claim 53 in which the dinitroaniline is pendimethalin.

75. The process of claim 53 in which the dinitroaniline is fluchloralin.

76. The process of claim 53 in which the dinitroaniline is profluralin.

77. The process of claim 53 in which the dinitroaniline is dinitramine.

78. The process of claim 53 in which the dinitroaniline is 4-trifluoromethyl-2,6-dinitro-3-chloro-N,N-diethylaniline.

* * * * *